US012632964B2

(12) United States Patent
Macaulay et al.

(10) Patent No.: US 12,632,964 B2
(45) Date of Patent: May 19, 2026

(54) SEQUENTIAL CONVOLUTIONAL NEURAL NETWORKS FOR NUCLEI SEGMENTATION

(71) Applicant: PROVINCIAL HEALTH SERVICES AUTHROITY, Vancouver (CA)

(72) Inventors: Calum Macaulay, Vancouver (CA); Paul Gallagher, Vancouver (CA)

(73) Assignee: Provincial Health Services Authority, Vancouver (CA)

( * ) Notice: Subject to any disclaimer, the term of this patent is extended or adjusted under 35 U.S.C. 154(b) by 349 days.

(21) Appl. No.: 18/339,193

(22) Filed: Jun. 21, 2023

(65) Prior Publication Data

US 2023/0410316 A1     Dec. 21, 2023

Related U.S. Application Data

(63) Continuation of application No. PCT/CA2022/050036, filed on Jan. 11, 2022.

(Continued)

(51) Int. Cl.
*G06T 7/11*     (2017.01)
*G06N 3/045*     (2023.01)
(Continued)

(52) U.S. Cl.
CPC ............... *G06T 7/11* (2017.01); *G06N 3/045* (2023.01); *G06N 3/08* (2013.01); *G06T 7/0012* (2013.01);
(Continued)

(58) Field of Classification Search
CPC . G06T 7/0012; G06T 7/11; G06T 7/12; G06T 7/70; G06T 2207/10056;
(Continued)

(56) References Cited

U.S. PATENT DOCUMENTS

2010/0111396 A1* 5/2010 Boucheron ............. G06F 18/29
                                                                    382/133
2013/0103618 A1* 4/2013 Urmanov ............... G06N 20/00
                                                                    706/20

(Continued)

OTHER PUBLICATIONS

Naylor et al., "Segmentation of Nuclei in Histopathology Images by Deep Regression of the Distance Map", IEEE Transactions on Medical Imaging, vol. 38, No. 2, Feb. 2019, pp. 448-459. (Year: 2019).*

(Continued)

*Primary Examiner* — Jennifer Mehmood
*Assistant Examiner* — Jose M Torres
(74) *Attorney, Agent, or Firm* — Todd A. Rattray; Oyen Wiggs Green & Mutala LLP

(57) ABSTRACT

Methods and apparatus for segmenting cell nuclei in medical images apply first and second trained machine learning algorithms. The first trained machine learning algorithm processes a medical image to provide center locations of cell nuclei depicted in the image. The second machine learning algorithm processes each of a plurality of patches of the image. Each of the patches correspond to one of the plurality of center locations. Processing each patch yields a nuclear boundary corresponding to the corresponding one of the center locations. The methods and apparatus allow associating individual pixels of the image with one or more than one nuclei and have been shown to be effective for instance segmentation of nuclei in clusters of overlapping cell nuclei.

23 Claims, 11 Drawing Sheets

Related U.S. Application Data

(60) Provisional application No. 63/136,567, filed on Jan. 12, 2021.

(51) Int. Cl.

| | |
|---|---|
| *G06N 3/08* | (2023.01) |
| *G06T 7/00* | (2017.01) |
| *G06T 7/12* | (2017.01) |
| *G06T 7/70* | (2017.01) |
| *G06V 10/82* | (2022.01) |
| *G06V 20/69* | (2022.01) |
| *G16H 30/40* | (2018.01) |

(52) U.S. Cl.
CPC .................. *G06T 7/12* (2017.01); *G06T 7/70* (2017.01); *G06V 10/82* (2022.01); *G06V 20/695* (2022.01); *G06V 20/698* (2022.01); *G16H 30/40* (2018.01); *G06T 2207/10056* (2013.01); *G06T 2207/20081* (2013.01); *G06T 2207/20084* (2013.01); *G06T 2207/30024* (2013.01)

(58) Field of Classification Search
CPC . G06T 2207/20021; G06T 2207/20081; G06T 2207/20084; G06T 2207/30024; G06N 3/045; G06N 3/0464; G06N 3/08; G06N 3/09; G06V 10/25; G06V 10/26; G06V 10/454; G06V 10/82; G06V 20/695; G06V 20/698; G16H 30/40
See application file for complete search history.

(56) References Cited

U.S. PATENT DOCUMENTS

| | | | | |
|---|---|---|---|---|
| 2015/0030219 | A1* | 1/2015 | Madabhushi | G06T 7/12 |
| | | | | 382/128 |
| 2016/0253466 | A1* | 9/2016 | Agaian | G06N 5/043 |
| | | | | 382/128 |
| 2019/0042826 | A1* | 2/2019 | Chang | G06T 7/11 |
| 2019/0258846 | A1* | 8/2019 | Dinov | G06V 20/64 |
| 2020/0090330 | A1* | 3/2020 | Chefd'hotel | G06T 7/0012 |
| 2020/0286233 | A1 | 9/2020 | Chefd'hotel et al. | |
| 2021/0407080 | A1* | 12/2021 | Szu | G16H 10/40 |
| 2022/0237789 | A1* | 7/2022 | Nie | G06F 18/2414 |

OTHER PUBLICATIONS

Vu et al., "Methods for Segmentation and Classification of Digital Microscopy Tissue Images", frontiers in Bioengineering and Biotechnology, Apr. 2, 2019, pp. 1-15. (Year: 2019).*

Ho et al., "Center-Extraction-Based Three Dimensional Nuclei Instance Segmentation of Fluorescence Microscopy Images", 2019.

He et al., "CellidNet: Automatic Cell Instance Segmentation and Classification in Bone Marrow Examination with Double Backbone Networks", 2020.

Evans et al., "US food and drug administration approval of whole slide imaging for primary diagnosis: A key milestone Is reached and new questions are raised", Apr. 2018.

Gertych et al., "Convolutional neural networks can accurately distinguish four histologic growth patterns of lung adenocarcinoma in digital slides", Feb. 2019.

Chang et al., "Artificial intelligence in pathology", Jan. 2019.

Kelly et al., "Key challenges for delivering clinical impact with artificial intelligence", 2019.

Holzinger et al., "What do we need to build explainable AI systems for the medical domain?", 2017.

Holzinger et al., "Towards the augmented pathologist: challenges of explainable-AI in digital pathology", 2017.

Ronneberger et al., "U-Net: Convolutional Networks for Biomedical Image Segmentation", 2015.

Zhou et al., "UNet++: A Nested U-Net Architecture for Medical Image Segmentation", Jul. 2018.

Abdolhoseini et al., "Segmentation of Heavily Clustered Nuclei from Histopathological Images", 2019.

Macaulay et al., "Adaptive color basis transformation. An aid in image segmentation", Feb. 1989.

Macaulay et al., "An edge relocation segmentation algorithm" Jun. 1990.

Zarei et al., "Automated prostate glandular and nuclei detection using hyperspectral imaging", 2017.

Zarei et al., "Introducing an Interactive Method to Improve Digital Pathology Image Segmentation: Case Study on Prostate Cancer", 2017.

Enfield et al., "Hyperspectral cell sociology reveals spatial tumor-immune cell interactions associated with lung cancer recurrence", Jan. 2019.

Guerrero-Pena et al., "Multiclass weighted loss for instance segmentation of cluttered cells", 2018.

Palcic et al., "Increase of sensitivity of sputum cytology using high-resolution image cytometry: field study results", Jun. 15, 2002;50(3):168-176.

Li et al., "Automated sputum cytometry for detection of intraepithelial neoplasias in the lung", 2012.

Macaulay et al., "High throughput image cytometry for detection of suspicious lesions in the oral cavity", Aug. 2012.

Keyes et al., "DNA ploidy measured on archived pretreatment biopsy material may correlate with prostate-specific antigen recurrence after prostate brachytherapy", Aug. 2013.

Chiu et al. "Quality Assurance System Using Statistical Process Control: An Implementation for Image Cytometry—Semantic Scholar", 2004.

Ikeda et al., "Malignancy associated changes in bronchial epithelial cells and clinical application as a biomarker", Mar. 1998.

Anderson et al., "The use of an automated image cytometer for screening and quantitative assessment of cervical esions in the British Columbia Cervical Smear Screening Programme", Oct. 1997.

Palcic et al., "Oncometrics Imaging Corp. and Xillix Technologies Corp.: Use of the Cyto-Savant in quantitative cytology", 1996.

Kamalov et al., "A Java Application for Tissue Section Image Analysis", 2005.

Levenson et al., "Spectral imaging in preclinical research and clinical pathology", 2013.

Marshall et al., "Establishing a cell sociology platform for the assessment of targetable interactions to predict lung cancer outcome", Sep. 2019.

Guillaud et al., "Potential use of Quantitative Tissue Phenotype to Predict Malignant Risk for Oral Premalignant Lesions", 2008.

Macaulay et al., "Quantification of large scale DNA organization for predicting prostate cancer recurrence", Dec. 2017.

Guillaud et al., "Large-scale DNA organization is a prognostic marker of breast cancer survival", Med Oncol. Dec. 2017.

Yeghiazaryan et al., "Family of boundary overlap metrics for the evaluation of medical image segmentation", Jan. 2018.

Wang et al., "Computational staining of pathology images to study the tumor microenvironment in lung cancer." 2020.

http://Ice.biohpc.swmed.edu/maskrenn/ "Computational staining of pathology images to study the tumor microenvironment in lung cancer", 2020, Web page.

Vuola et al., "Mask-RCNN and U-net Ensembled for Nuclei Segmentation", Jan. 2019.

Hofener et al., "Deep Learning Nuclei Detection: A Simple Approach Can Deliver State-of-the-Art Results", Feb. 2018.

* cited by examiner

SEQUENTIAL CONVOLUTIONAL NEURAL NETWORKS FOR NUCLEI SEGMENTATION

CROSS-REFERENCE TO RELATED APPLICATIONS

This application is a continuation of Patent Cooperation Treaty (PCT) application No. PCT/CA2022/050036 having an international filing date of 11 Jan. 2022, which in turn claims priority from, and for the purposes of the United States of America the benefit of 35 U.S.C. § 119 in connection with, U.S. application No. 63/136,567 filed 12 Jan. 2021 and entitled SEQUENTIAL CONVOLUTIONAL NEURAL NETWORKS FOR NUCLEI SEGMENTATION. All of the applications referred to in this paragraph are hereby incorporated herein by reference for all purposes.

FIELD

The present invention relates to image recognition and to histology. Example embodiments provide automatic segmentation of cell nuclei in images of tissue sections.

BACKGROUND

There is a need for better ways to detect neoplastic diseases such as cancer and to assess the likely progress of such diseases. Histopathology (the microscopic study of diseased tissue) has been the gold standard for cancer diagnosis and prognosis for over 100 years. In histopathology thin (typically several μm thick) tissue sections are reviewed by specialist physicians who may observe patterns that allow them to characterize the observed tissue. The observed patterns result from the aggregate are effects of molecular alterations on cell behavior and represent phenotypic information that has been found to be correlated to certain disease states and to expected outcomes. For the neoplastic process this information provides a convenient visual readout of disease state and aggressiveness.

Whole slide scanning has enabled the creation of digital pathology representations (digital images) of the entire section that normally would be examined visually through a microscope. These digital representations of the tissue are sufficiently accurate that expert visual interpretation of the digital images (as opposed to direct microscopic examination of the tissue samples themselves) has been approved for use in some patient diagnosis (Ref. 1).

It would be beneficial to take advantage of computer-aided analysis to make processing of histology specimens more efficient and possibly also to discover novel features to predict cancer behavior (outcomes) and to improve understanding of the neoplastic process.

A range of machine learning (ML) technologies have been applied in an attempt to provide systems capable of automatic classification of tissues, identification of diseases and assessment of the progress of diseases. All machine learning methods applied to images form intermediate representations of the observed data and extract information from those representations. However, it is often difficult or impossible to interpret features of the intermediate representations themselves. It can therefore be difficult to achieve a level of trust in such ML systems that is sufficient to justify relying on such systems in cases where a person's health is at stake.

Deep Learning (DL) using some form of Convolutional Neural Networks (CNN) have been successfully applied to images of sectioned tissue to recognize cancer, stage cancer and even to predict biological aggressiveness of the cancers from which the tissue came (Ref 2). While some DL has demonstrated the ability to perform as well as or better than expert pathologists for the recognition and classification of cancerous tissue, the DL only produces the answer it was trained to recognize and does not easily offer additional information (Refs 2,3). The general consensus is that the black box nature of many DL-based systems does not inspire trustworthiness which will be an impediment to clinical adoption. Thus explainable-AI, "Interpretability" of how the DL comes to its conclusions has become an area of active research(4,5).

Characteristics of cell nuclei tend to be important phenotypic information. However, it is challenging to make a practical image processing system capable of reliably automatically segmenting cell nuclei in digital pathology representations. One reason for this is that digital pathology representations often include clusters of overlapping cell nuclei such that individual pixels may correspond to zero, one or plural nuclei. Additional complicating factors include intensity variations caused by noise and uneven absorption of stains.

Robust accurate segmentation of cell nuclei for overlapping nuclei clusters is one of the most significant unsolved issues in digital pathology. A segmentation algorithm as accurate as human annotators would be a great enabler for many fields of research and clinical utility in digital pathology. It would in fact be transformative to the field. Increased cell density associated with dysregulated growth is frequently where interesting cancer biology takes place and because of the increased cell density the likelihood of cell overlaps is much higher and quantitative analysis is traditionally more difficult to perform.

Despite progress that has been made in the field of image recognition and digital pathology there remains a need for improved and alternative technologies for segmenting cell nuclei in digital pathology representations.

SUMMARY

The present invention provides methods and apparatus for automatic segmentation of cell nuclei in digital histopathology representations (DHR mages). In example embodiments the methods and apparatus apply separate ML algorithms in sequence. A first ML algorithm determines locations of cell nuclei in a DHR image. A second ML algorithm processes a patch around each of the determined locations to determine a boundary of a corresponding cell nucleus.

One example aspect of the invention provides a method for segmenting cell nuclei in medical images. The medical images may, for example be digital histopathology representations, cytology images, cytopathology images, or in vivo histology images (obtained by any modality). The method comprises: by a first trained machine learning algorithm processing a medical image to provide center locations of cell nuclei depicted in the medical image; and by a second trained machine learning algorithm processing each of a plurality of patches of the medical image, each of the patches corresponding to one of the plurality of center locations, the processing by the second trained machine learning algorithm outputting a nuclear boundary corresponding to the corresponding one of the center locations.

In some embodiments the first machine learning algorithm is implemented by a first convolutional neural network. In some embodiments the first convolutional neural network has a UNet configuration. In some embodiments the UNet configuration comprises 5 or more layers. In some embodiments the first convolutional neural network has a configuration selected from UNet++, Mask R-CNN, FastFCN, Gated—SCNN, and DeepLab.

In some embodiments, processing each of the plurality of patches of the medical image by the second machine learning algorithm comprises receiving each of the patches as input to a second convolutional neural network. In some embodiments the second convolutional neural network has a UNet configuration. In some embodiments the second convolutional neural network has a configuration selected from UNet++, Mask R-CNN, FastFCN, Gated—SCNN, and DeepLab.

In some embodiments the patches are equal in size. In some embodiments the patches of the medical image are centered on the corresponding one of the plurality of center locations. In some embodiments the patches of the digital histopathology representation are square. In some embodiments the patches of the digital histopathology representation have dimension of at least 80 by 80 pixels. In some embodiments the patches of the digital histopathology representation have dimension of at least 128 by 128 pixels.

In some embodiments the first machine learning algorithm is implemented by a first convolutional neural network, the second machine learning algorithm is implemented by a second convolutional neural network and the first and second convolutional neural networks have architectures that are different from one another.

In some embodiments the first machine learning algorithm is implemented by a first convolutional neural network, the second machine learning algorithm is implemented by a second convolutional neural network and the first and second convolutional neural networks have architectures that are the same as one another.

In some embodiments the method further comprises obtaining cell information corresponding to the center locations and processing the cell information together with the center locations to perform cell type based cell-cell association quantification. The cell information may, for example, comprise morphologically based and/or immunohistochemistry (IHC) based characterization information.

In some embodiments the medical image includes one or more clusters of overlapping cell nuclei.

In some embodiments the method further comprises applying feature calculations and a binary classification tree to classify objects corresponding to the nuclear boundaries.

Another aspect of the invention provides apparatus for segmenting cell nuclei in medical images. The medical images may, for example be digital histopathology representations, cytology images, cytopathology images, or in vivo histology images (obtained by any modality). The apparatus comprises: a first trained machine learning algorithm operative to process a medical image to provide center locations of cell nuclei depicted in the medical image; and a second trained machine learning algorithm operative to process each of a plurality of patches of the medical image, each of the patches corresponding to one of the plurality of center locations, the processing by the second trained machine learning algorithm outputting a nuclear boundary corresponding to the corresponding one of the center locations.

In some embodiments the first machine learning algorithm is implemented by a first convolutional neural network. In some embodiments the first convolutional neural network has a UNet configuration.

In some embodiments the UNet configuration comprises 5 or more layers. In some embodiments the first convolutional neural network has a configuration selected from UNet++, Mask R-CNN, FastFCN, Gated—SCNN, and DeepLab.

In some embodiments the second machine learning algorithm is configured to receive each of the patches as input to a second convolutional neural network. In some embodiments the second convolutional neural network has a UNet configuration. In some embodiments the second neural network has five or more layers. In some embodiments the second convolutional neural network has a configuration selected from UNet++, Mask R-CNN, FastFCN, Gated—SCNN, and DeepLab.

In some embodiments the patches are equal in size. In some embodiments the patches of the medical image are centered on the corresponding one of the plurality of center locations. In some embodiments the patches of the digital histopathology representation are square. In some embodiments the patches of the digital histopathology representation have dimension of at least 80 by 80 pixels. In some embodiments the patches of the digital histopathology representation have dimension of at least 128 by 128 pixels.

In some embodiments the first machine learning algorithm is implemented by a first convolutional neural network, the second machine learning algorithm is implemented by a second convolutional neural network and the first and second convolutional neural networks have architectures that are different from one another.

In some embodiments the first machine learning algorithm is implemented by a first convolutional neural network, the second machine learning algorithm is implemented by a second convolutional neural network and the first and second convolutional neural networks have architectures that are the same as one another.

In some embodiments The apparatus further comprises a data processor configured to obtain cell information corresponding to the center locations and processing the cell information together with the center locations to perform cell type based cell-cell association quantification. The data processor optionally also implements one or both of the first and second machine learning algorithms. The cell information may, for example, comprise morphologically based and/or immunohistochemistry (IHC) based characterization information.

In some embodiments the apparatus is operable to instance segment individual cell nuclei in one or more clusters of overlapping cell nuclei included in the medical image.

In some embodiments the apparatus comprises a data processor configured to apply one or more feature calculations and a binary classification tree to classify objects corresponding to the nuclear boundaries.

Other aspects of the invention provide apparatus having any new and inventive feature, combination of features, or sub-combination of features as described herein and/or methods having any new and inventive steps, acts, combination of steps and/or acts or sub-combination of steps and/or acts as described herein.

Further aspects and example embodiments are illustrated in the accompanying drawings and/or described in the following description.

It is emphasized that the invention relates to all combinations of the above features with one another and with any features described elsewhere herein, even if these are recited in different claims.

BRIEF DESCRIPTION OF THE DRAWINGS

The accompanying drawings illustrate non-limiting example embodiments of the invention.

DETAILED DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive sense.

The present technology provides methods and apparatus for automated cell nucleus segmentation. Here "segmentation" involves identifying individual cell nuclei. Once individual nuclei have been identified, characteristics of the nuclei may be quantified.

A general approach applied by the present technology is to use sequential rounds of processing by two different trained convolutional neural networks (CNNs). In the following examples the CNNs have a UNet architecture.

The inventors have determined that the sequential application of two separate CNNs can facilitate reparsing an original image into multiple overlapping sub images. This feature explicitly allows for the present technology to perform a one pixel mapping to many objects (e.g. plural nuclei). An additional benefit of allowing a one to many assignment of pixels, is that the complete shapes (boundaries) of the nuclei can be more accurately identified since the same pixel(s) in an image may be assigned to multiple nuclei involved in the area of their overlap.

The inventors have found that on images with highly complex overlapping clusters of nuclei prototype implementations of the present technology were able to correctly segment more (10-20%, image complexity dependent)

nuclei than other methods in areas of high complexity. In addition the prototype implementations were able to recognize and segment large numbers of nuclei completely missed by the other methods.

More recent prototype implementations trained using larger training data sets demonstrated segmentation accuracy on a 200K plus nuclei validation set at 92%.

Figure 1:
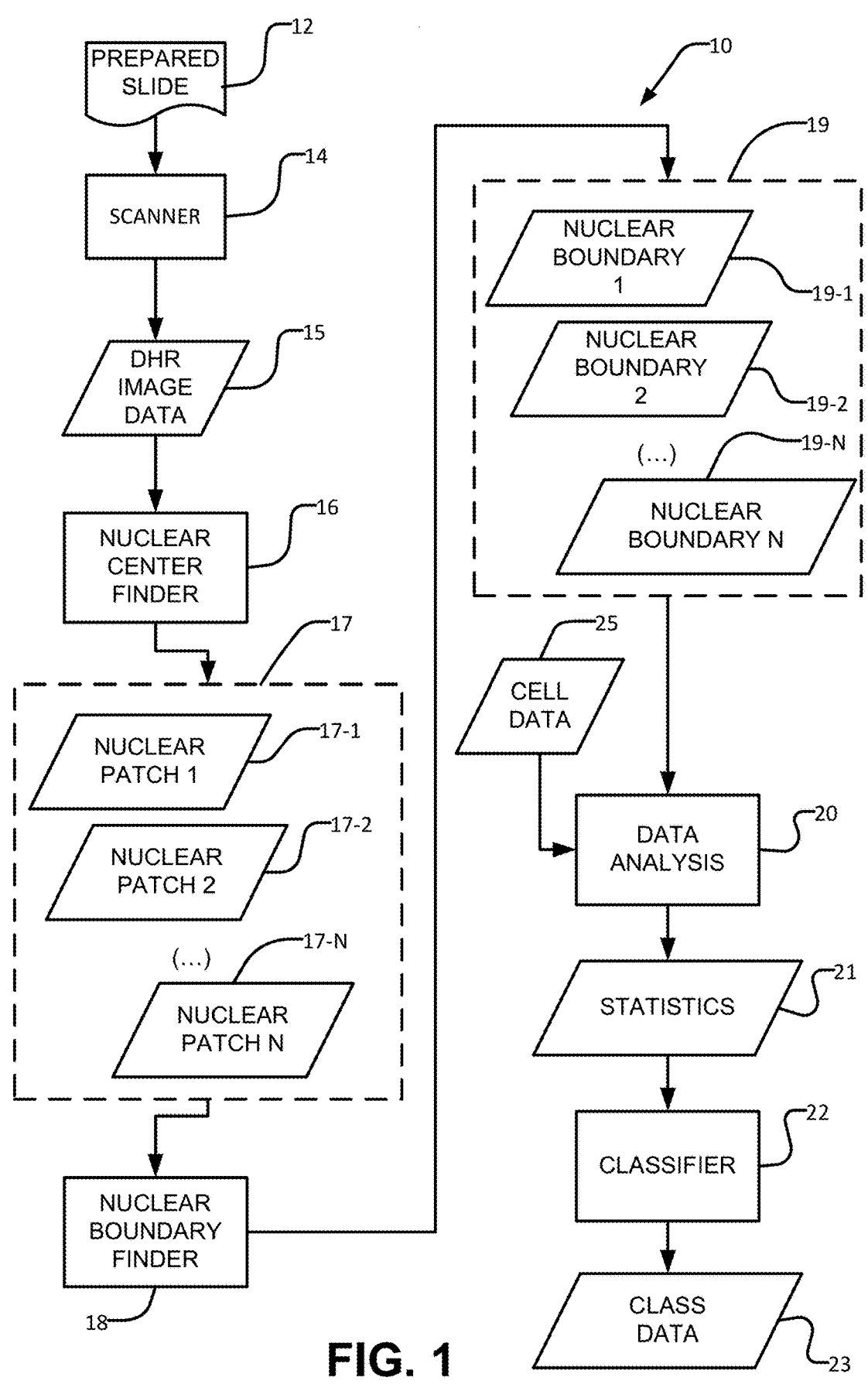
FIG. 1 is a block diagram that shows apparatus according to an example embodiment as well as a flow of a method according to an example embodiment of the invention.

FIG. 1 is a block diagram of example apparatus 10 according to the invention. FIG. 1 also illustrates flow of an example method according to the invention. Apparatus 10 comprises a scanner 14 that is operative to scan a slide 12 to yield image data 15 for a digital histology representation (DHR). Slide 12 may for example comprise a thin tissue sample. The tissue sample may be prepared (e.g. by a suitable stain—for example thionin or hematoxylin) to enhance visibility of nuclei in the tissue sample. Scanner 14 may comprise a suitable commercial histology slide scanner for example. Histology slide scanners are commercially available from several suppliers.

Figure 1A:
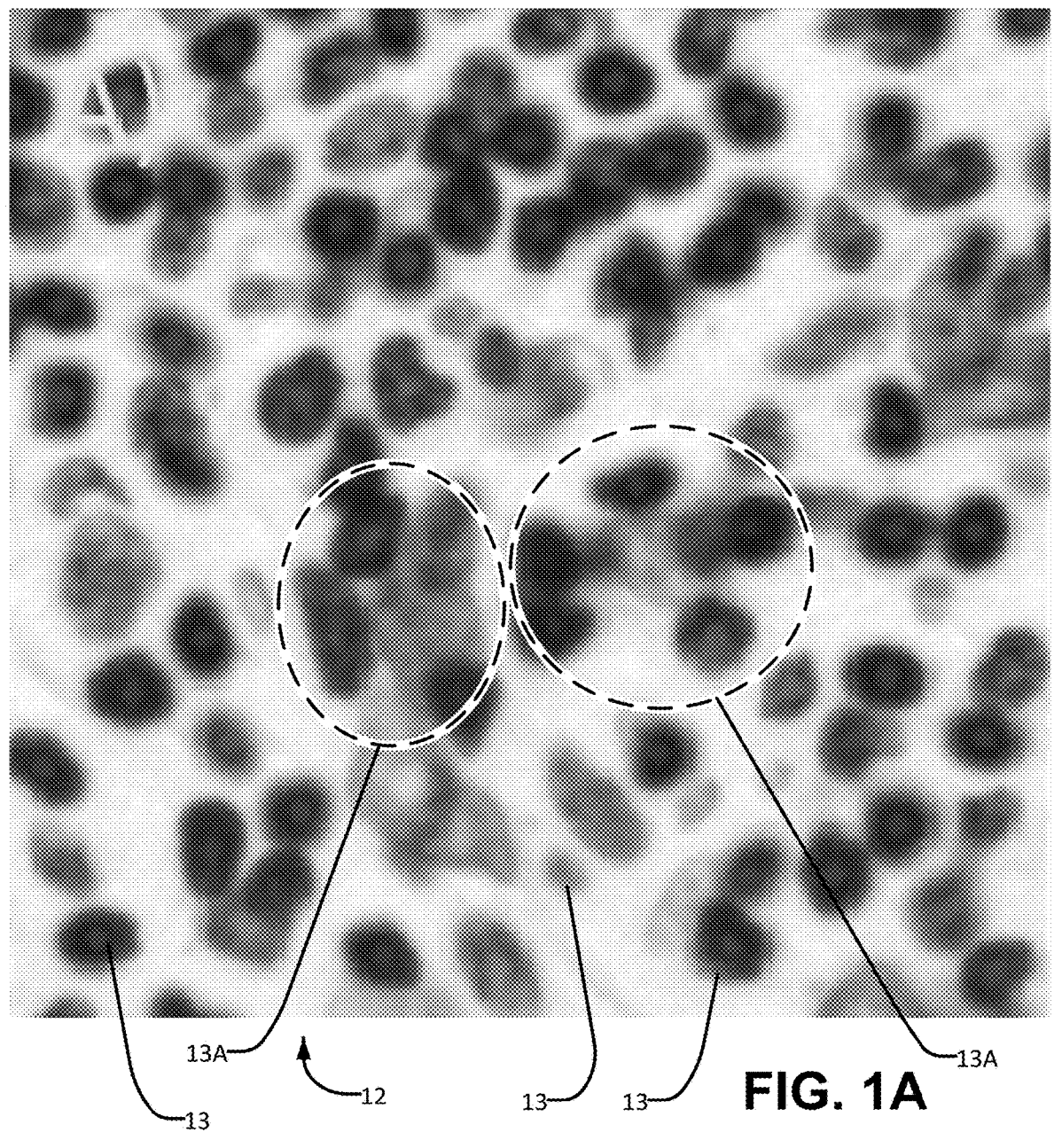
FIG. 1A is a portion of an image of a histology slide in which cell nuclei have been stained.

FIG. 1A is a partial image of a slide 12 containing an example histology section. A histology section is composed of a tissue slice (a 3D collection of cells and parts of cells). The thickness of the section is typically on the same order of many of the components (nuclei, chromosomes, mitochondria, cell membranes) or much larger (proteins, lipids, etc.). Almost all of these are transparent to visible light. The tissue components may be visualized by labeling them (e.g. with a stain such as a suitable chromophore or fluorophore). For an imaging microscope the data collected is a projection of light through all or some of the sectioned stained tissue. It is highly likely that at least some pixels in the image contain information from two or more cells or cellular components. In slide 12 nuclei 13 of cells have been stained. Slide 12 includes several areas (e.g. 13A) in which plural nuclei 13 overlap with one another.

DHR image data 15 is provided as input to a nuclear center finder 16 which is operative to fine centers of nuclei depicted in DHR image data 15. Nuclear center finder 16 may, for example comprise a trained machine learning (ML) system such as a trained CNN.

Nuclear center finder 16 outputs patches 17 from DHR image data 15 which each correspond to a located center of a cell nucleus. If centers of N cell nuclei are found by nuclear center finder 16, then nuclear center finder 16 may output N patches (17-1, 17-2 . . . 17-N). Each patch 17 includes the corresponding nuclear center determined by nuclear center finder 16. The corresponding nuclear center is consistently located in patches 17. For example, the corresponding nuclear center may be located at the center of each patch 17. For example, each patch 17 may be a square patch centered on a nuclear center determined by nuclear center finder 16.

Patches 17 are dimensioned to be large enough to include boundaries of the corresponding nuclei. The minimum sizes for patches 17 depends on the resolution of DHR image data 15, optical magnification provided by scanner 14 and the actual sizes of nuclei in the tissue of slide 12. In a prototype embodiment patches 17 have sizes of 128 by 128 pixels.

Patches 17 are provided as input to a nuclear boundary finder 18. Nuclear boundary finder 18 may, for example comprise a trained ML system such as a trained CNN. For each patch 17, nuclear boundary finder 18 outputs boundary data 19 indicating a boundary for the corresponding cell nucleus. Boundary data 19 includes data 19-1, 19-2, 19-N which each provides a boundary for one cell nucleus corresponding to one of patches 17-1, 17-2 . . . 17-N.

Optional data analyzer 20 processes boundary data 19 and outputs statistics 21. Data analyzer 20 may, for example, output statistics data 21 indicative of one or more of:

statistics (e.g. mean, median, standard deviation) of the areas of nuclei depicted in DHR image data 15;

statistics regarding the shapes (e.g. eccentricity) of nuclei depicted in DHR image data 15;

statistics regarding the length and/or tortuosity and/or curvatures of boundaries of nuclei depicted in DHR image data 15;

statistics regarding the spatial distribution of nuclei depicted in DHR image data 15;

etc.

Statistics data 21 may be provided as input to a further system 22 that processes statistics data 21 to yield indications of likely pathologies for the tissue of slide 12 and/or the likely future development of a pathology. System 22 may output class information 23.

In some embodiments additional cell information 25 for cells depicted in DHR image 15 is supplied to data analyzer 20. Cell information 25 may, for example comprise cell characterization information (e.g. morphologically based and/or immunohistochemistry (INC) based characterization). In such embodiments data analyzer 20 may perform cell type based cell-cell association quantification.

It is possible but not necessary that CNNs that are used to implement nuclear center finder 16 and nuclear boundary finder 18 be of the same type. In some embodiments the CNNs used to implement nuclear center finder 16 and nuclear boundary finder 18 are of different types. In a prototype system the CNNs used to implement nuclear center finder 16 and nuclear boundary finder 18 each had a UNet architecture. However, either or both nuclear center finder 16 and nuclear boundary finder 18 could be implemented by a CNN having an alternative architecture such as UNet++, Mask R-CNN, FastFCN, Gated—SCNN, DeepLab and others.

Methods for training CNNs are well understood by those of skilled in the art and are not described herein in detail. CNNs used to implement nuclear center finder 16 and/or nuclear boundary finder 18 may, for example be trained using iterative training which, in a training loop, optimizes weights in convolutional layers (learnable parameters) of the CNNs by minimizing a value of a loss function using gradients of the loss function with respect to the learnable parameters. The gradients may be determined from a model gradients function.

Example Prototype System

CNNs and Deep learning has demonstrated an ability to recognize objects as well as or better than humans. While most CNNs result in a classification or call for the image, there are a subset that can define the pixels involved in the object sought. Such CNNs can perform semantic segmentation or instance segmentation. UNet/UNet++ is one such CNN structure (Refs. 7,8,15). UNet is a form of CNN that can recognize specific objects and mark their boundaries once identified.

Figure 2:
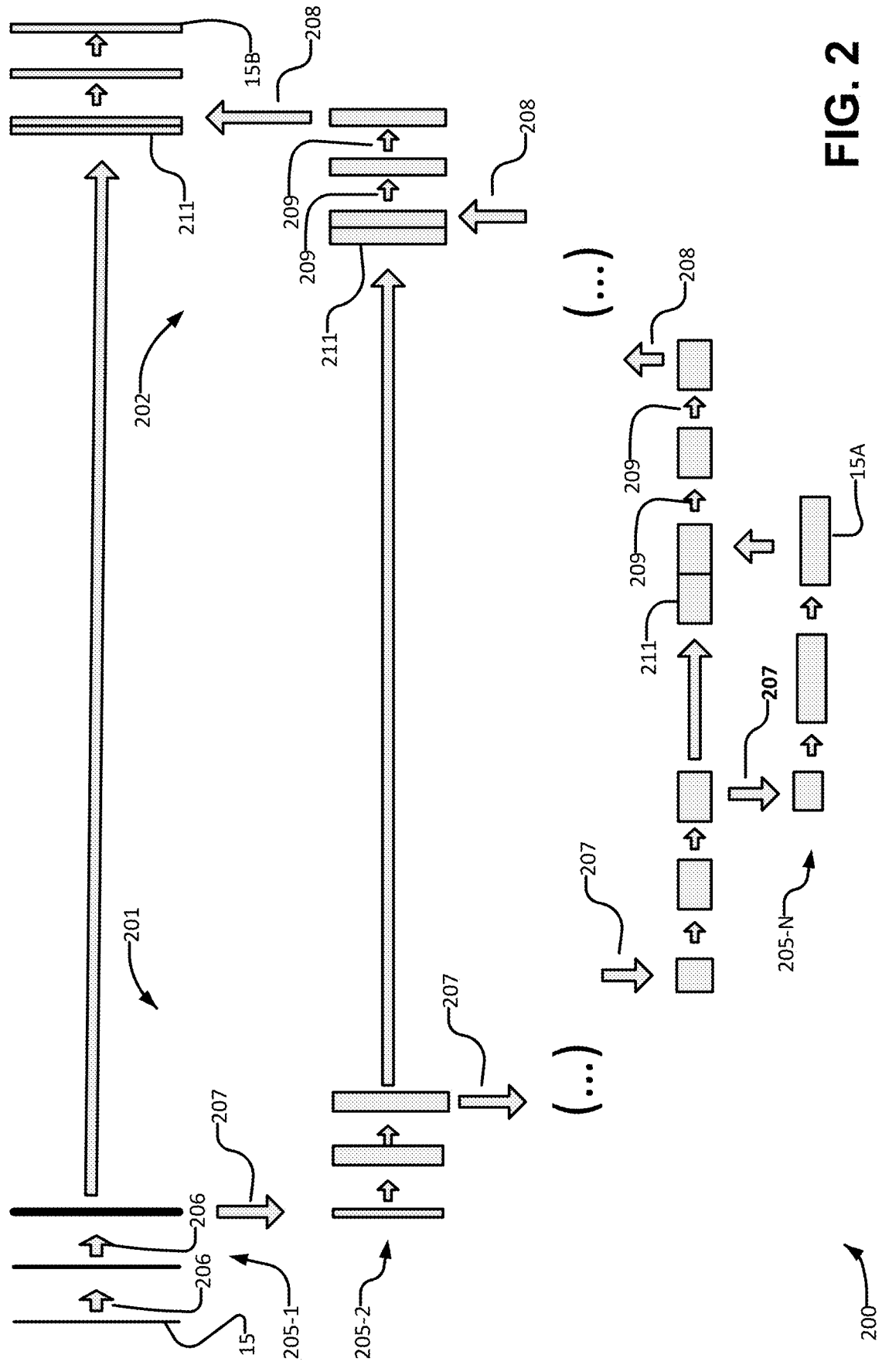
FIG. 2 is a block diagram showing an example structure of a UNet convolutional neural network.

FIG. 2 shows an example architecture for a UNet CNN 200. CNN 200 includes a contracting path or encoder 201 that receives DHR image data 15 and, over a series of levels 205-1, 205-2, . . . 205-N applies convolution layers 206 and max pooling 207 to produce a reduced size and increased depth intermediate representation 15A of DHR image data 15.

An expanding path or decoder 202 applies a series of levels that perform upsampling 208 and apply convolutional layers 209 to increase the size of intermediate representation 15A to produce an output image 15B. At each level a feature map 211 from encoder 201 is passed to decoder 202 and concatenated with an upsampled representation. CNN 200 may have any suitable number of layers and different numbers of convolution blocks in each layer.

In a prototype embodiment UNet CNNs having the general architecture shown in FIG. 2 were used to implement each of nuclear center finder 16 and nuclear boundary finder 18. Each of these CNNs had 5 levels with 2 layers of convolution blocks in each level. The number of convolutions in each block is doubled in every level starting from 32 (32, 64, 128, 256, 512 and back up again 256, 128, 64, 32). For the prototype implementation 3 by 3 convolutions were used everywhere except for the first two blocks of level 1 in the nuclear center finder 16 where it was found to be advantageous to use 5 by 5 convolutions and in the nuclear boundary finder 18 where it was found to be advantageous to use 5 by 5 convolutions for the first two levels of the encoding part (downwards, left side of the UNet) and in the final level of the decoding side (upwards right side of the UNet).

The UNet used to implement nuclear center finder 16 is configured by suitable training to identify the geometric centers of all nuclei within an image such as DHR image 15 (FIG. 1).

Using the nuclei geometric centers output by nuclear center finder 15, multiple patches centered on the previously identified nuclei geometric centers are selected from the DHR image 15. In the prototype the patches were each 128 by 128 pixel images however, patches of other suitable sizes could be used. It is desirable that the patches be large enough that the boundary of all or substantially all of any cell nucleus of interest that is depicted in DHR image 15 will lie within the patch when the geometric center of the cell nucleus is centered in the patch.

The UNet used to implement nuclear boundary finder 18 is configured by suitable training to identify the nuclear boundary for only the nucleus which is centered in each of these patch images.

The division between center finding and boundary finding and reparsing the original image into multiple potentially overlapping sub images explicitly allows for mapping of one pixel in an image such as a DHR image to many objects. It was found that providing patch images to nuclear boundary finder 18 which are aligned with corresponding nuclei (e.g. the center of a corresponding nucleus is at a predetermined location in patch image) facilitates accurate identification of the corresponding nuclear boundary even where the corresponding nucleus is part of a cluster of nuclei that overlap in DHR image 15.

In a prototype system used to demonstrate operation of the present technology included an AMD based computer workstation with an Nvidia 2070 based graphics card which was used to accelerate CNN calculations. UNet CNNs as described herein were implemented on this computer workstation. The prototype system was able to segment the nuclei in an entire prostate needle biopsy specimen section in 2-3 minutes.

Example Training Data

Another aspect of the invention relates to training of CNNs (e.g. UNet CNNs) that may be used to implement nuclear center finder 16 and nuclear boundary finder 18. A CNN may be trained to identify the geometric centers of all nuclei within a DHR image 15 using training data (e.g. DHR images in which cell nuclei and their geometric centers have been labelled.

Since, in a typical DHR image only relatively few pixels happen to lie at the geometric center of a cell nucleus, there is a large class imbalance between positive (cell nucleus center pixels) vs non-cell-nucleus center pixels a large amount of training data may be required to train a CNN used for nuclear center finder 16. An available set of training data may be augmented by creating altered training data as is known in the art. For example, a labelled DHR image that can be used as training data may be transformed (e.g. by one or more of scaling, rotation, tone mapping, geometric distortion, one or more morphological operations such as dilation and/or erosion etc.) to yield altered images that may be used as additional training data. Training may be performed in multiple rounds.

The inventors have found that creating altered training data by eroding nuclear boundaries can be particularly effective. For example, starting training of a CNN with annotated images (e,g, DHR images in which nuclei have been annotated by mask pixels, for example by human inspection of the DHR images) in the first round followed by multiple training rounds using ever more eroded versions of the masks are used as training data until only the center pixels remained was found to result in consistently successful nuclei center identification.

The inventors had access to training data sets showing normal cells, abnormal cells, and immune cells as well as training data sets depicting junk cells/debris/overlapping nuclei. These training data sets contain well over 2 million human annotated objects (See Ref. 22). Some of this training data was used in training the prototype system.

Generating training data for the prototype system was facilitated by in house developed tools which facilitate acquiring, reviewing and annotating DHR images. These tools include automated image cytometry systems for the scanning of cytology samples (Cervix, Lung, Oral) (see Refs 16-24). These systems are operable to automatically load slides and collect images of every object in best focus.

The tools also included software systems that are operable to analyze detected objects, automatically sort and classify them into: normal cells; abnormal cells; immune cells; junk cells; debris; and overlapping nuclei and present the detected objects for human review and classification. These tools are useful for building training data sets and also for final human review of any detected abnormal cells detected prior to signing off a slide as abnormal or normal (See Refs. 23,24).

The tools include an interface that allows a user to trace boundaries of cell nuclei or other objects—for example by dragging a cursor along the boundary—as well as to annotate areas of overlap of different displayed objects (e.g. cell nuclei).

The reproducibility of boundaries of cell nuclei drawn by different human annotators is not as high as one might expect. This disagreement likely comes from the difficulty in exactly tracing the boundary of a nucleus by hand, especially where a boundary being traced is for a nucleus in a complex cluster of nuclei. A training data set may be improved by including in training data training images in which the same cell nuclei have been traced by multiple different human reviewers and/or by refining traced images using software which adjusts the boundaries over a very limited range (e.g. 1 or 2 pixels) to most closely follow the edge (rapid intensity change) of an object. For example, the drawn boundaries may be snapped to the strongest edge within a few pixels. These approaches or a combination of them may yield more consistent boundaries in training data sets and, in turn improved accuracy in a system trained using the training data sets.

Figure 4:
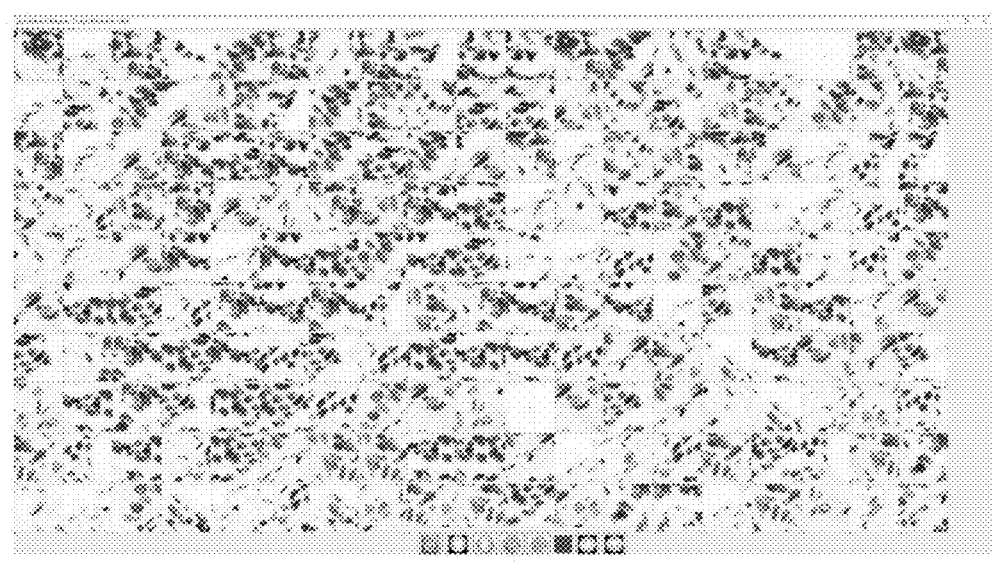
FIG. 4 shows an example user interface for a tool useful for viewing and annotating DHR images.

FIG. 4 is a screen shot of a graphical user interface for an example tool useful for reviewing the segmentation/classification of 1000's of nuclei rapidly. The controls along the bottom allow one to: page forward or back, jump to the end of images or the start, display all images or only those from a specific group, toggle the display of the nuclear boundaries and zoom in or zoom out.

The present technology may be integrated into a tool of the general type described for example in Refs 23 and 24 to provide automated segmentation of cell nuclei.

Figure 6A:
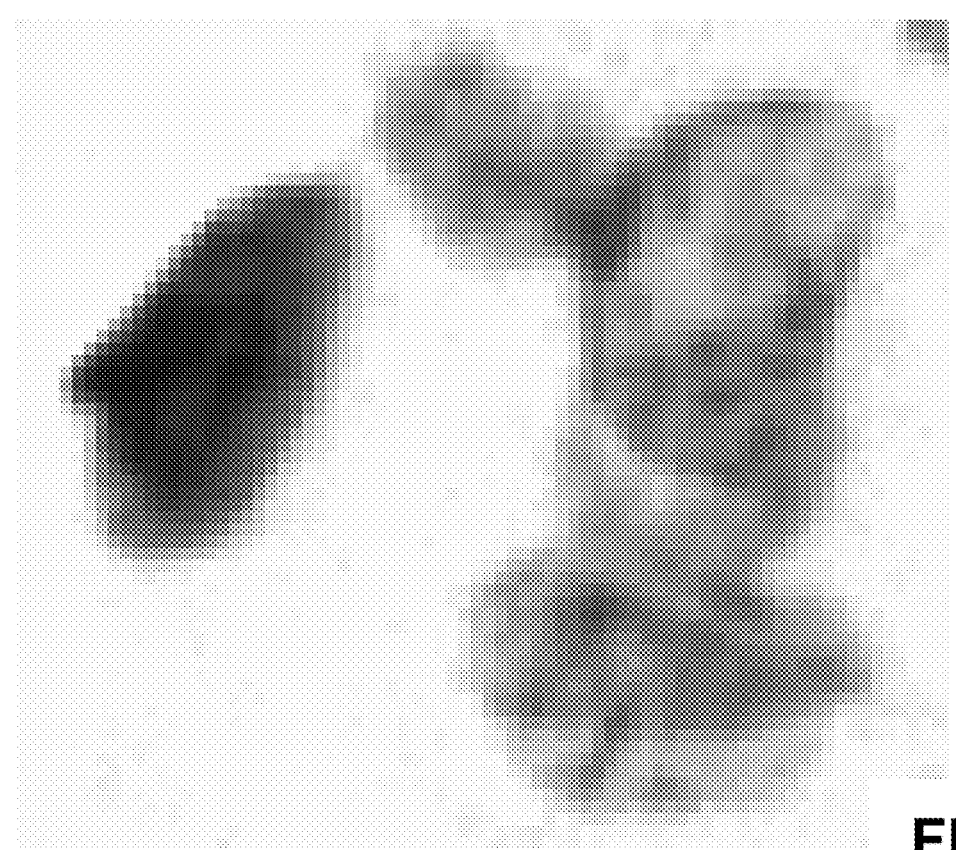
FIGS. 6A, 6B and 6C are respectively a section of a DHR image showing a cluster of cell nuclei, the section of the image marked to show boundaries of the cell nuclei in the cluster and a mask showing the boundaries only.
Figure 6B:
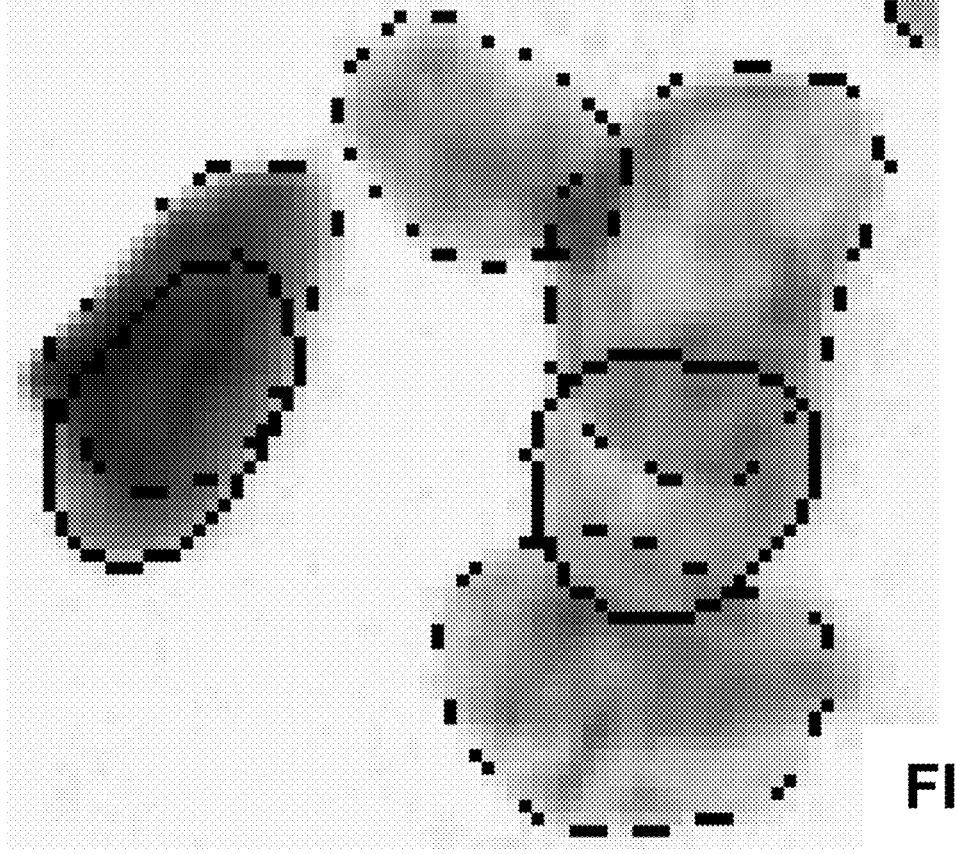
Figure 6C:
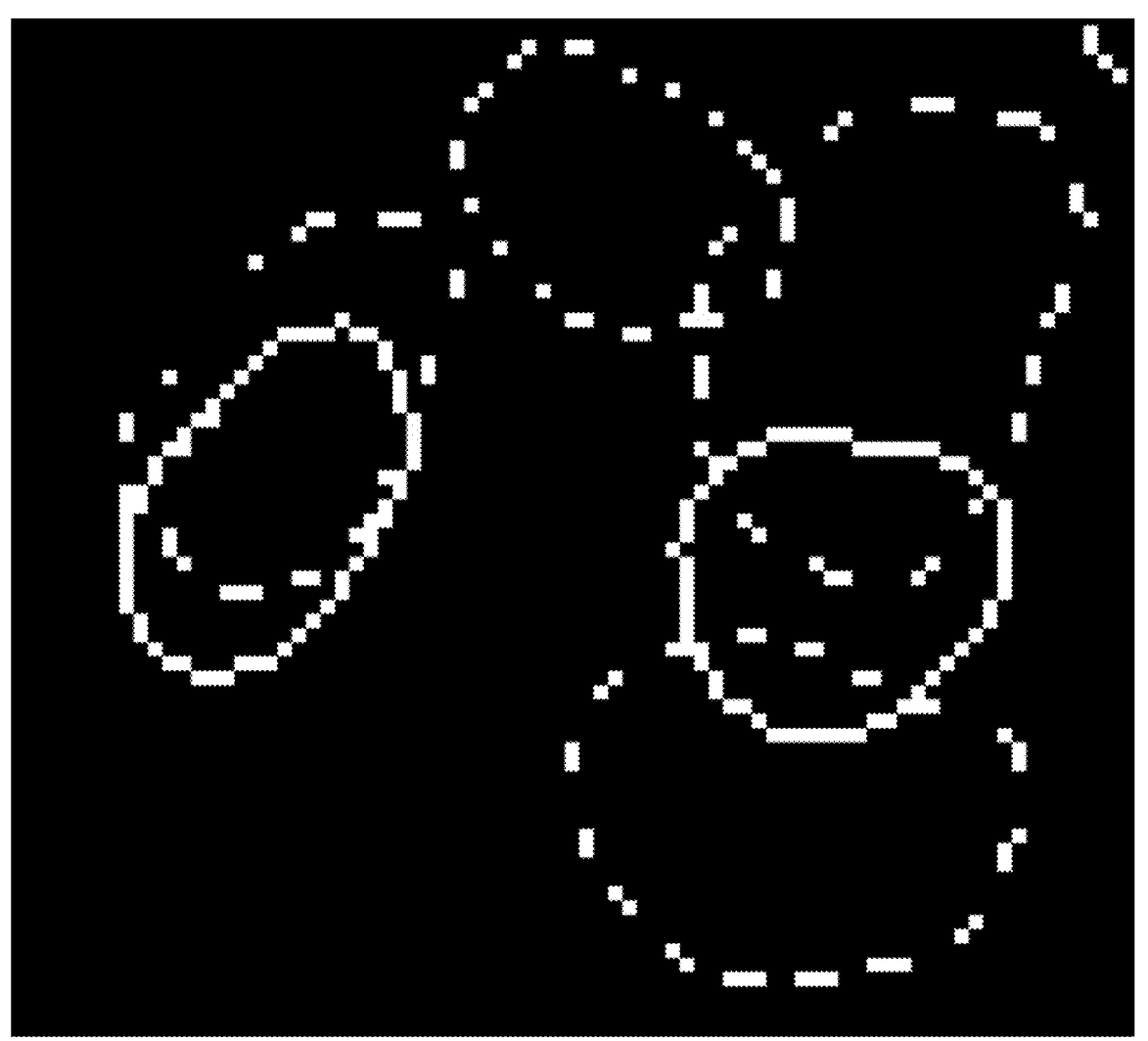
Figure 7C:
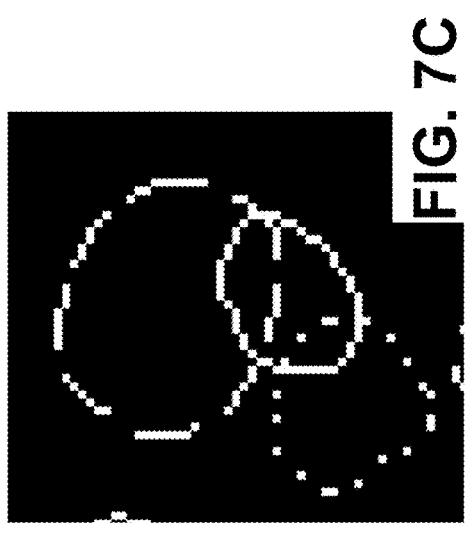
FIGS. 7A, 7B and 7C are respectively a section of a DHR image showing a cluster of cell nuclei, the section of the image marked to show boundaries of the cell nuclei in the cluster and a mask showing the boundaries only.
Figure 8C:
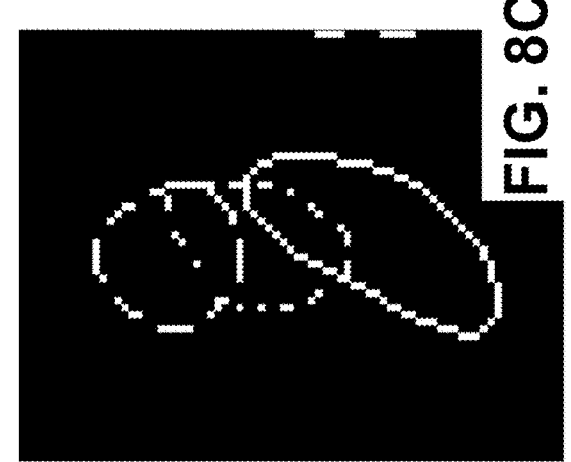
FIGS. 8A, 8B and 8C are respectively a section of a DHR image showing a cluster of cell nuclei, the section of the image marked to show boundaries of the cell nuclei in the cluster and a mask showing the boundaries only.
Figure 7B:
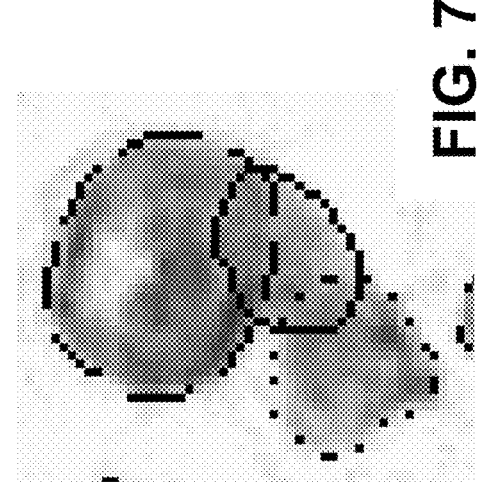
Figure 8B:
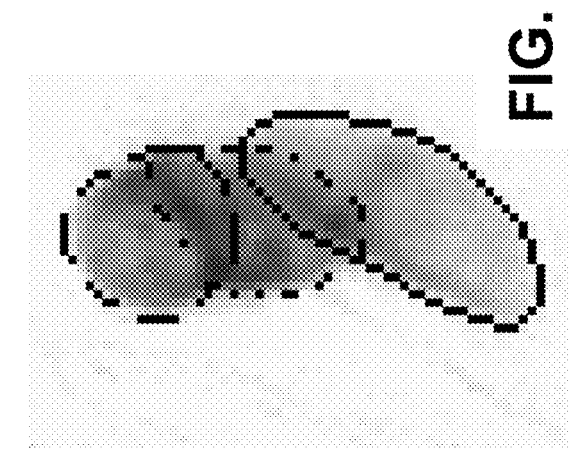
Figure 7A:
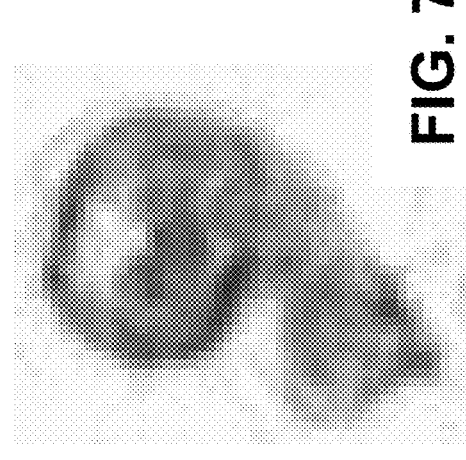
Figure 8A:
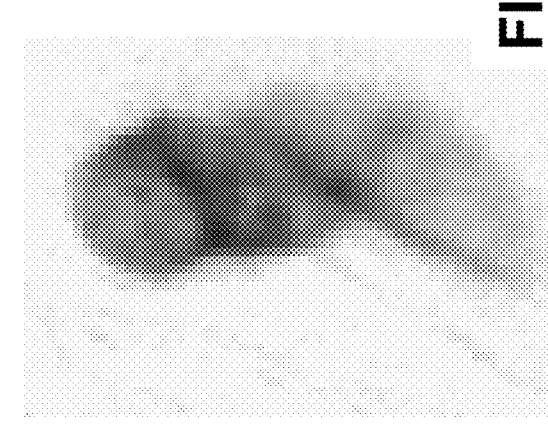

FIGS. 6A to 6C are respectively a section of a DHR image showing a cluster of cell nuclei, the section of the image marked to show boundaries of the cell nuclei in the cluster and a mask showing the boundaries only. The boundaries shown in FIGS. 6B and 6C may, for example be drawn by a human using a suitable tool (e.g. a tool as shown in FIG. 4). These boundaries may be included in training data for a CNN used to implement nuclear boundary finder 18. A loss function used in training the CNN may be based on differences between the boundaries shown in FIGS. 6B and 6C from boundaries determined by the CNN used to implement nuclear center finder 18.

FIGS. 7A to 7C and 8A to 8C are similar to FIGS. 6A to 6C but show different clusters of cell nuclei.

Example Results

Figures 3A, 3B:
FIG. 3A is an example DHR image that includes cell nuclei marked with center locations that have been determined by a nuclear center finder.
FIG. 3B is an example training DHR image marked to show cell nuclei that have been eroded to generate additional training data.

FIG. 3A shows the results of a UNet trained to recognize the centers of nuclei. The light spots at the centers of the depicted nuclei are the geometric centers of the nuclei as determined by the UNet CNN. The success rate on a set of 28,000 training nuclei (with data augmentation) was found to be 95%-90% (depending upon human evaluator) which is much better than conventional ML algorithms on the same images. In the further developed prototype which was trained using a larger training data set segmentation accuracy on a 200K plus nuclei validation was 92% for all objects. Feature calculations and a binary classification tree were then applied to classify objects (as cell nuclei and other objects). After this classification, 99.2% of objects classified as nuclei were found to be well segmented cell nuclei regardless of size or shape. The classification tree weeded out (e.g. classified as not being nuclei) segmentation failures and objects too small and/or to light to be nuclei.

FIG. 3B shows example eroded nucleus masks as used to train the UNet to identify the geometric centers of nuclei depicted in DHR images. In FIG. 3B the nucleus masks are partially eroded. Training data may include images in which the nucleus masks are less eroded than as shown in FIG. 3B as well as images in which the nucleus masks are more eroded than as shown in FIG. 3B.

Figure 3C:
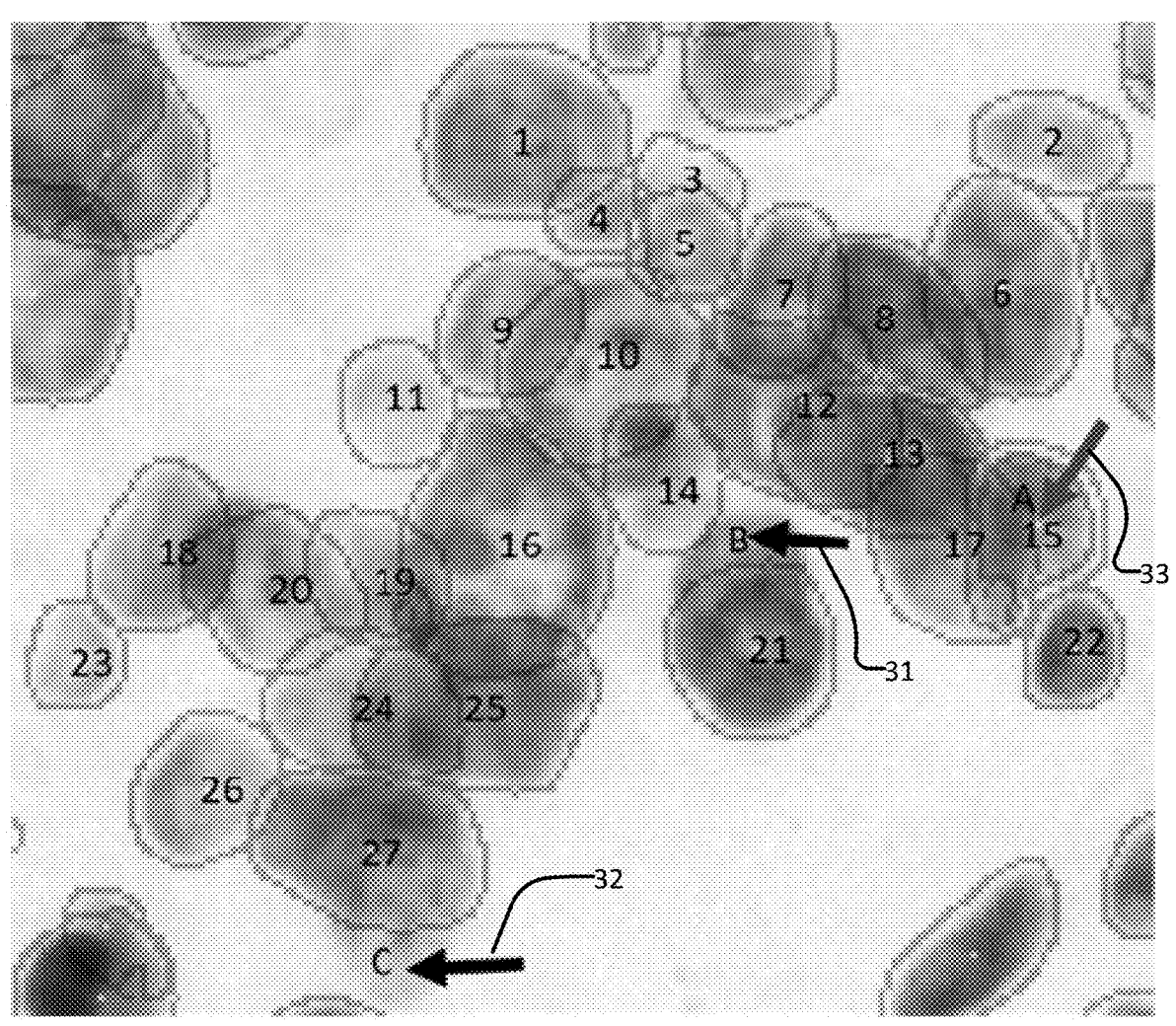
FIGS. 3C and 3D are portions of DHR images that have been marked to show nuclear centers and nuclear boundaries determined by a prototype system.
Figure 3D:
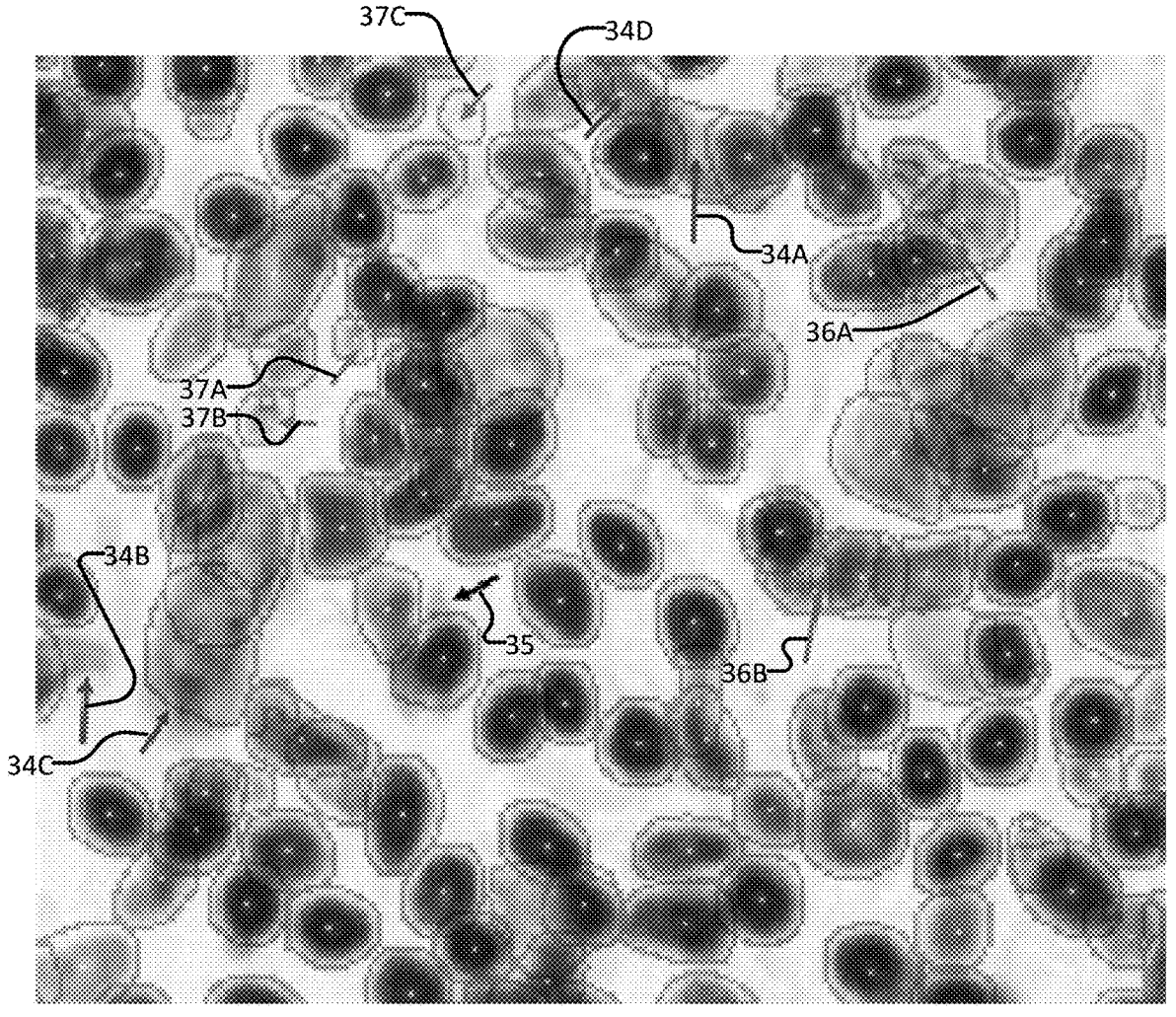

FIGS. 3C and 3D show example results of the prototype system on two test sub images from much larger tissue microarray (TMA) images. These sub images include complex overlapping clusters of nuclei.

FIG. 3C shows a cluster of thirty cell nuclei all of which have similar absorption, pixel darkness). The prototype system correctly segmented all but three of the depicted nuclei. The first UNet (implementing nuclear center finder 16) missed two of the thirty nuclei indicated by arrows 31 and 32. The second UNet (implementing nuclear boundary finder 18) missed segments of the 15th nucleus as indicated by arrow 33. The results in FIG. 3C demonstrate ~90% correct segmentation (~as it is hard to tell if the nucleus labelled 12 is segmented correctly).

FIG. 3D shows several clusters in which the absorption pixel darkness varies significantly over the depicted nuclei. In this image the prototype system also achieved ~90% accuracy in segmenting the nuclei.

FIG. 3D depicts approximately 97 nuclei. Of these, four nuclei as indicated by arrows (34A, 34B, 34C and 34D) were not correctly segmented. One nucleus was missed (indicated by arrow 35). Two false nuclear centers (indicated by arrows 36A and 36B) were incorrectly identified. Three objects that may not be cell nuclei (they are too small and/or too light in tone) were identified as indicated by arrows 37A, 37B and 37C.)

On a set 12,522 nuclei from TMA spots that were not included in training data used to train the UNet CNNs of the prototype the segmentation performed by the prototype had an accuracy in the range of 58-93% correct segmentation rate. The accuracy varied depending on the nature of the depicted nuclei. The segmentation accuracy for long thin stromal cell nuclei was about 58%. The segmentation accuracy for epithelial and immune cell nuclei was about 93%. The segmentation accuracy over the total set of TMA spots was about 84%. As discussed above, a subsequent prototype implementation in which much larger training sets were used to train nuclear center finder 16 and nuclear boundary finder 18 had even higher accuracy.

For cell types not well represented in the training set, the segmentation of new nuclei of that type was not as accurate as for cell types that were well represented in the training data.

Figure 5:
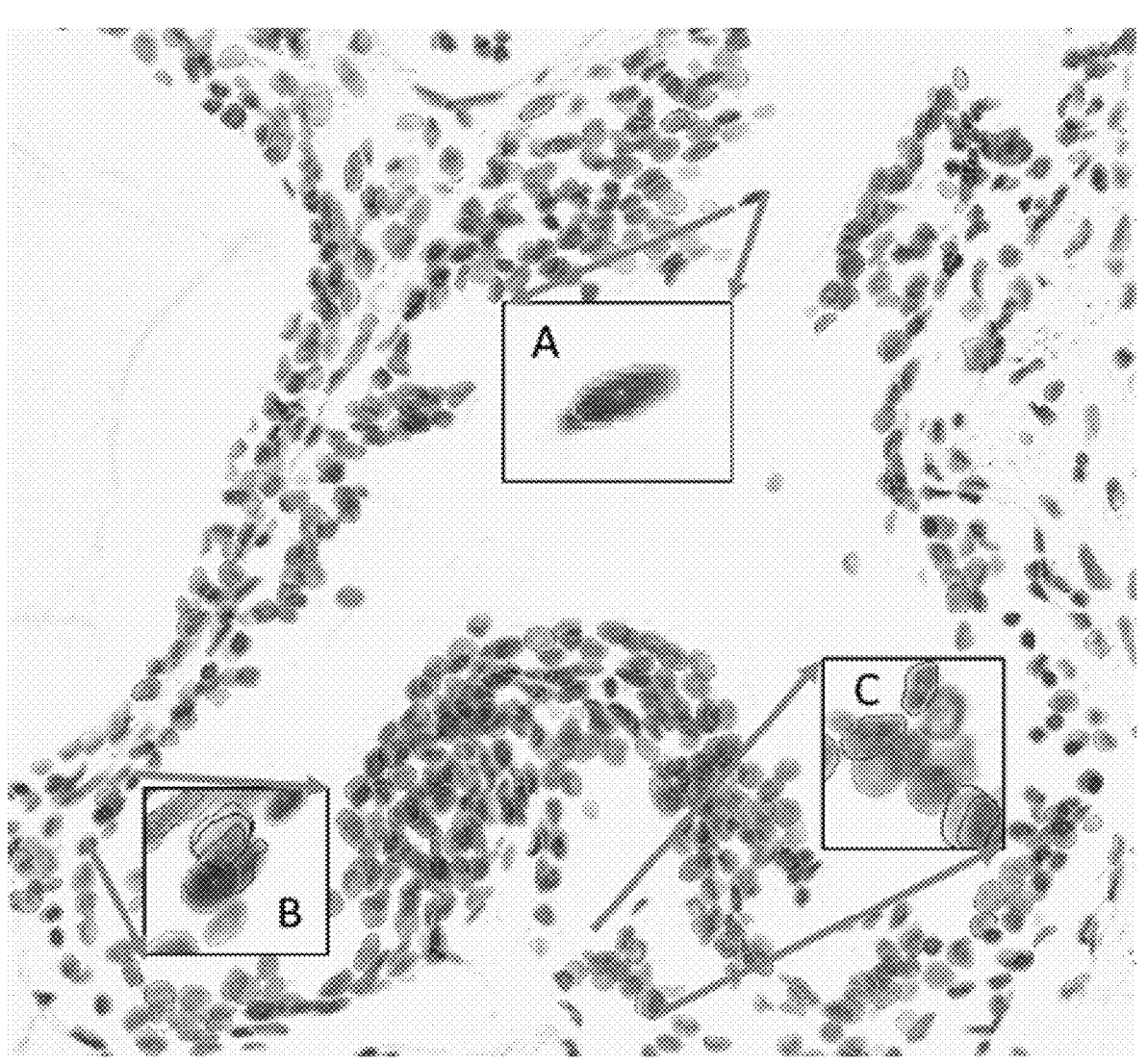
FIG. 5 is an example portion of a DHR image that has been marked to show nuclear centers and nuclear boundaries determined by a prototype system.

FIG. 5 shows results of segmentation of cell nuclei in a DHR image of prostate tissue using the prototype system. The DHR image was of a thionin-stained prostate needle biopsy applied to an independent prostate section. The three inserts show some example errors. It is believed that the likelihood of such errors can be reduced by improved training of CNNs used to implement nuclear center finder 16 and/or nuclear boundary finder 18. In insert A the prototype system did not properly identify the entire boundary of a long thin nucleus. Errors of this type may be reduced or avoided by including sufficient examples of long thin nuclei in training data used to train CNNs in nuclear center finder 16 and/or nuclear boundary finder 18. Insert B shows over-segmentation of a cluster of nuclei. This can arise where nuclear center finder 16 over identifies a number of centers of nuclei in the nuclei cluster. In FIG. 5 the nuclear cluster associated with insert B is slightly out of focus. This out of focus condition may tend to make over segmentation more likely. Insert C demonstrates an error that is opposite to the error of insert B. In insert C nuclear center finder 16 is failing to detect some of nuclei present in the corresponding cluster. To make a system as described herein more resilient to errors of the types illustrated in inserts B and C, training data for nuclear center finder 16 and/or nuclear boundary finder 18 may include subsets of the training images that are highly enriched with annotated images similar to the errors observed that can be used as "finishing training sets" to improve the optimization of the networks' weights for theses segmentation instances.

Example Applications

The present technology may be applied to determine locations of cells in tissue. In some embodiments this location information is combined with cell characterization information (e.g. morphologically based and/or immunohistochemistry (IHC) based characterization). This combination allows for cell type based cell-cell association quantification. This will enhance the fidelity of the intermediate representation (cell types, cell location, cell-cell associations) of the tissue. These intermediate representations can be used by subsequent ML/DL steps for tissue classification as well as for improving our understanding of the development of diseases such as cancers.

Some embodiments enable the creation of accurate spatial cell level representations of tissue based upon molecular single cell analysis of each cell in the tissue. This methodology may be scaled up to the entire tissue section level in a way that is amiable to high throughput clinical scale efforts.

Intermediate representations of the tissue can be based upon the cellular building blocks of the tissue itself and thus improve interpretability of the process. For example, nuclear center finder 16 operates to recognize the cells and structures within the cells that make up the tissue and where each is located. With this information one can then categorize the cells into various types based upon their morphological and molecular characteristics. These cell locations and characteristics can then be fed into a second CNN/ML algorithm to generate the final cell/tissue classification. This approach has the very large benefit that it allows for "Interpretability" of the intermediate representations used by the DL/CNN/ML process in the context of the large literature knowledge base of our current understanding of the neoplastic process and its interaction with the hosts tissues and immune system.

The use of cell locations and characteristics allows for another large benefit the "Standardization" of the intermediate representation data (normalization of magnification, stain variation and other device specific effects using methods that have already exist in the digital pathology knowledge base) which should improve the generalizability of the DL results (6).

An advantage of at least some embodiments of the present technology is that intermediate representations created in processing DHR images may be more closely associated with physical properties of the tissue represented in the DHR images than is the case in other ML systems.

The foregoing examples have illustrated application of the present technology to segmenting cell nuclei in DHR images. It can be appreciated that the technology may be used for instance segmentation of other transparent or partially transparent overlapping objects of which cells and cell nuclei are examples. For example, the present technology may be applied to segmenting cells and/or cell nuclei in "medical images" which include: cytology images, cytopathology images, in vivo histology images (obtained by any modality) and histopathology images such as DHR images.

Where a component (e.g. a software module, processor, assembly, device, circuit, etc.) is referred to herein, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Embodiments of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs"). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors.

In typical applications, nuclear center finder 16 and nuclear boundary finder 18 are implemented in a programmed computer which includes a graphics processor unit (GPU) which is programmed by computer executable instructions to perform calculations for determining output from CNNs.

The invention may also be provided in the form of a program product. The program product may comprise any non-transitory medium which carries a set of computer-readable instructions which, when executed by a data processor, cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or preprogrammed chips (e.g., EEPROM semiconductor chips), nanotechnology memory, or the like. The computer-readable signals on the program product may optionally be compressed or encrypted.

Interpretation of Terms

Unless the context clearly requires otherwise, throughout the description and the claims:

"comprise", "comprising", and the like are to be construed in an inclusive sense, as opposed to an exclusive or exhaustive sense; that is to say, in the sense of "including, but not limited to";

"connected", "coupled", or any variant thereof, means any connection or coupling, either direct or indirect, between two or more elements; the coupling or connection between the elements can be physical, logical, or a combination thereof;

"herein", "above", "below", and words of similar import, when used to describe this specification, shall refer to this specification as a whole, and not to any particular portions of this specification;

"or", in reference to a list of two or more items, covers all of the following interpretations of the word: any of the items in the list, all of the items in the list, and any combination of the items in the list;

the singular forms "a", "an", and "the" also include the meaning of any appropriate plural forms. These terms ("a", "an", and "the") mean one or more unless stated otherwise;

"and/or" is used to indicate one or both stated cases may occur, for example A and/or B includes both (A and B) and (A or B);

"approximately" when applied to a numerical value means the numerical value ±10%;

where a feature is described as being "optional" or "optionally" present or described as being present "in some embodiments" it is intended that the present disclosure encompasses embodiments where that feature is present and other embodiments where that feature is not necessarily present and other embodiments where that feature is excluded. Further, where any combination of features is described in this application this statement is intended to serve as antecedent basis for the use of exclusive terminology such as "solely," "only" and the like in relation to the combination of features as well as the use of "negative" limitation(s)" to exclude the presence of other features; and "first" and "second" are used for descriptive purposes and cannot be understood as indicating or implying relative importance or indicating the number of indicated technical features.

Words that indicate directions such as "vertical", "transverse", "horizontal", "upward", "downward", "forward", "backward", "inward", "outward", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Where a range for a value is stated, the stated range includes all sub-ranges of the range. It is intended that the statement of a range supports the value being at an endpoint of the range as well as at any intervening value to the tenth of the unit of the lower limit of the range, as well as any subrange or sets of sub ranges of the range unless the context clearly dictates otherwise or any portion(s) of the stated range is specifically excluded. Where the stated range includes one or both endpoints of the range, ranges excluding either or both of those included endpoints are also included in the invention.

Certain numerical values described herein are preceded by "about". In this context, "about" provides literal support for the exact numerical value that it precedes, the exact numerical value ±5%, as well as all other numerical values that are near to or approximately equal to that numerical value. Unless otherwise indicated a particular numerical value is included in "about" a specifically recited numerical value where the particular numerical value provides the substantial equivalent of the specifically recited numerical value in the context in which the specifically recited numerical value is presented. For example, a statement that something has the numerical value of "about 10" is to be interpreted as: the set of statements:

in some embodiments the numerical value is 10;
in some embodiments the numerical value is in the range of 9.5 to 10.5;

and if from the context the person of ordinary skill in the art would understand that values within a certain range are substantially equivalent to 10 because the values with the range would be understood to provide substantially the same result as the value 10 then "about 10" also includes:

in some embodiments the numerical value is in the range of C to D where C and D are respectively lower and upper endpoints of the range that encompasses all of those values that provide a substantial equivalent to the value 10

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

As will be apparent to those of skill in the art upon reading this disclosure, each of the individual embodiments described and illustrated herein has discrete components and features which may be readily separated from or combined with the features of any other described embodiment(s) without departing from the scope of the present invention.

Any aspects described above in reference to apparatus may also apply to methods and vice versa.

Any recited method can be carried out in the order of events recited or in any other order which is logically possible. For example, while processes or blocks are presented in a given order, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, simultaneously or at different times.

Various features are described herein as being present in "some embodiments". Such features are not mandatory and may not be present in all embodiments. Embodiments of the invention may include zero, any one or any combination of two or more of such features. All possible combinations of such features are contemplated by this disclosure even where such features are shown in different drawings and/or described in different sections or paragraphs. This is limited only to the extent that certain ones of such features are incompatible with other ones of such features in the sense that it would be impossible for a person of ordinary skill in the art to construct a practical embodiment that combines such incompatible features. Consequently, the description that "some embodiments" possess feature A and "some embodiments" possess feature B should be interpreted as an express indication that the inventors also contemplate embodiments which combine features A and B (unless the description states otherwise or features A and B are fundamentally incompatible). This is the case even if features A and B are illustrated in different drawings and/or mentioned in different paragraphs, sections or sentences.

The invention has a number of non-limiting aspects. Non-limiting aspects of the invention include:

1. A method for segmenting cell nuclei in medical images, the method comprising:

by a first trained machine learning algorithm processing a medical image to provide center locations of cell nuclei depicted in the medical image;

by a second trained machine learning algorithm processing each of a plurality of patches of the medical image, each of the patches corresponding to one of the plurality of center locations, the processing by the second trained machine learning algorithm outputting a nuclear boundary corresponding to the corresponding one of the center locations.

2. The method according to aspect 1 wherein the first machine learning algorithm is implemented by a first convolutional neural network.

3. The method according to aspect 2 wherein the first convolutional neural network has a UNet configuration.

4. The method according to aspect 3 wherein the UNet configuration comprises 5 or more layers.

5. The method according to aspect 2 wherein the first convolutional neural network has a configuration selected from UNet++, Mask R-CNN, FastFCN, Gated—SCNN, and DeepLab.

6. The method according to any of aspects 1 to 5 wherein processing each of the plurality of patches of the medical image by the second machine learning algorithm comprises receiving each of the patches as input to a second convolutional neural network.

7. The method according to aspect 6 wherein the second convolutional neural network has a UNet configuration.

8. The method according to aspect 6 wherein the second convolutional neural network has a configuration selected from UNet++, Mask R-CNN, FastFCN, Gated—SCNN, and DeepLab.

9. The method according to any of aspects 1 to 8 wherein the patches are equal in size.

10. The method according to any of aspects 1 to 9 wherein the patches of the medical image are centered on the corresponding one of the plurality of center locations.

11. The method according to any of aspects 1 to 10 wherein the patches of the digital histopathology representation are square.

12. The method according to any of aspects 1 to 11 wherein the patches of the digital histopathology representation have dimension of at least 80 by 80 pixels.

13. The method according to any of aspects 1 to 11 wherein the patches of the digital histopathology representation have dimension of at least 128 by 128 pixels.

14. The method according to aspect 1 wherein the first machine learning algorithm is implemented by a first convolutional neural network, the second machine learning algorithm is implemented by a second convolutional neural network and the first and second convolutional neural networks have architectures that are different from one another.

15. The method according to aspect 1 wherein the first machine learning algorithm is implemented by a first convolutional neural network, the second machine learning algorithm is implemented by a second convolutional neural network and the first and second convolutional neural networks have architectures that are the same as one another.

16. The method according to any of aspects 1 to 15 further comprising obtaining cell information corresponding to the center locations and processing the cell information together with the center locations to perform cell type based cell-cell association quantification.

17. The method according to aspect 16 wherein the cell information comprises morphologically based and/or immunohistochemistry (INC) based characterization information.

18. The method according to any one of aspects 1 to 16 wherein the medical image comprises: a digital histopathology representation, a cytology image, a cytopathology image, or an in vivo histology image.

19. The method according to any of aspects 1 to 18 wherein the medical image includes one or more clusters of overlapping cell nuclei.

20. The method according to any of aspects 1 to 19 comprising applying feature calculations and a binary classification tree to classify objects corresponding to the nuclear boundaries.

21. Apparatus for segmenting cell nuclei in medical images, the apparatus comprising:

a first trained machine learning algorithm operative to process a medical image to provide center locations of cell nuclei depicted in the medical image;

a second trained machine learning algorithm operative to process each of a plurality of patches of the medical image, each of the patches corresponding to one of the plurality of center locations, the processing by the second trained machine learning algorithm outputting a nuclear boundary corresponding to the corresponding one of the center locations.

22. The apparatus according to aspect 21 wherein the first machine learning algorithm is implemented by a first convolutional neural network.

23. The apparatus according to aspect 22 wherein the first convolutional neural network has a UNet configuration.

24. The apparatus according to aspect 23 wherein the UNet configuration comprises 5 or more layers.

25. The apparatus according to aspect 22 wherein the first convolutional neural network has a configuration selected from UNet++, Mask R-CNN, FastFCN, Gated—SCNN, and DeepLab.

26. The apparatus according to any of aspects 21 to 25 wherein the second machine learning algorithm is configured to receive each of the patches as input to a second convolutional neural network.

27. The apparatus according to aspect 26 wherein the second convolutional neural network has a UNet configuration.

28. The apparatus according to aspect 26 wherein the second convolutional neural network has a configuration selected from UNet++, Mask R-CNN, FastFCN, Gated—SCNN, and DeepLab.

29. The apparatus according to any of aspects 21 to 28 wherein the patches are equal in size.

30. The apparatus according to any of aspects 21 to 29 wherein the patches of the medical image are centered on the corresponding one of the plurality of center locations.

31. The apparatus according to any of aspects 21 to 30 wherein the patches of the digital histopathology representation are square.

32. The apparatus according to any of aspects 21 to 31 wherein the patches of the digital histopathology representation have dimension of at least 80 by 80 pixels.

33. The apparatus according to any of aspects 21 to 31 wherein the patches of the digital histopathology representation have dimension of at least 128 by 128 pixels.

34. The apparatus according to aspect 21 wherein the first machine learning algorithm is implemented by a first convolutional neural network, the second machine learning algorithm is implemented by a second convolutional neural network and the first and second convolutional neural networks have architectures that are different from one another.

35. The apparatus according to aspect 21 wherein the first machine learning algorithm is implemented by a first convolutional neural network, the second machine learning algorithm is implemented by a second convolutional neural network and the first and second convolutional neural networks have architectures that are the same as one another.

36. The apparatus according to any of aspects 21 to 35 further comprising a data processor configured to obtain cell information corresponding to the center locations and processing the cell information together with the center locations to perform cell type based cell-cell association quantification.

37. The apparatus according to aspect 36 wherein the cell information comprises morphologically based and/or immunohistochemistry (INC) based characterization information.

38. The apparatus according to any one of aspects 21 to 37 wherein the medical image comprises: a digital histopathology representation, a cytology image, a cytopathology image, or an in vivo histology image.

39. The apparatus according to any of aspects 21 to 38 wherein the apparatus is operable to instance segment individual cell nuclei in one or more clusters of overlapping cell nuclei included in the medical image.

40. The apparatus according to any of aspects 21 to 39 comprising a data processor configured to apply one or more feature calculations and a binary classification tree to classify objects corresponding to the nuclear boundaries.

41. Apparatus having any new and inventive feature, combination of features, or sub-combination of features as described herein.

42. Methods having any new and inventive steps, acts, combination of steps and/or acts or sub-combination of steps and/or acts as described herein.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

REFERENCES

1. ADDIN F1000_CSL_BIBLIOGRAPHY Evans A J, Bauer T W, Bui M M, Cornish T C, Duncan H, Glassy E F, et al. US food and drug administration approval of whole slide imaging for primary diagnosis: A key milestone is reached and new questions are raised. Arch Pathol Lab Med. 2018 Apr. 30; 142(11):1383-1387.

2. Gertych A, Swiderska-Chadaj Z, Ma Z, Ing N, Markiewicz T, Cierniak S, et al. Convolutional neural networks can accurately distinguish four histologic growth patterns of lung adenocarcinoma in digital slides. Sci Rep. 2019 Feb. 6; 9(1):1483.

3. Chang H Y, Jung C K, Woo J I, Lee S, Cho J, Kim S W, et al. Artificial intelligence in pathology. J Pathol Transl Med. 2019 January; 53(1):1-12.

4. Kelly, C. J., Karthikesalingam, A., Suleyman, M. et al. Key challenges for delivering clinical impact with artificial intelligence. *BMC Med* 17, 195 (2019). https://doi.org/10.1186/s12916-019-1426-2

5. Holzinger, A., Biemann, C., Pattichis, C. S., Kell, D. B.: What do we need to build explainable AI systems for the medical domain? arXiv:1712.09923 (2017)

6. Holzinger, A., et al.: Towards the augmented pathologist: challenges of explainable-AI in digital pathology. arXiv: 1712.06657 (2017)

US 12,632,964 B2

19

20

7. Ronneberger O, Fischer P, Brox T. U-Net: Convolutional Networks for Biomedical Image Segmentation. In: Navab N, Hornegger J, Wells W M, Frangi A F, editors. Medical Image Computing and Computer-Assisted Intervention—MICCAI 2015. Cham: Springer International Publishing; 2015. p. 234-241.

8. Zongwei Zhou, Md Mahfuzur Rahman Siddiquee, Nima Tajbakhsh, and Jianming Liang. UNet++: A Nested U-Net Architecture for Medical Image Segmentation. arXiv: 1807.10165.

9. Abdolhoseini, M., Kluge, M. G., Walker, F. R. et al. Segmentation of Heavily Clustered Nuclei from Histopathological Images. Sci Rep 9,4551 (2019). https://doi.org/10.1038/s41598-019-38813-2

10. MacAulay C, Tezcan H, Palcic B. Adaptive color basis transformation. An aid in image segmentation. Anal Quant Cytol Histol. 1989 February; 11(1):53-58.

11. MacAulay C, Palcic B. An edge relocation segmentation algorithm. Anal Quant Cytol Histol. 1990 June; 12(3): 165-171.

12. Zarei N, Bakhtiari A, Gallagher P, Keys M, MacAulay C. Automated prostate glandular and nuclei detection using hyperspectral imaging. 2017 IEEE 14th International Symposium on Biomedical Imaging (ISBI 2017). IEEE; 2017. p. 1028-1031.

13. Zarei N, Bakhtiari A, Korbelik J, Carraro A, Keyes M, MacAulay C. Introducing an Interactive Method to Improve Digital Pathology Image Segmentation: Case Study on Prostate Cancer. Anal Quant Cytopathology Histpathol. 2017; 39:1-16.

14. Enfield K S S, Martin S D, Marshall E A, Kung S H Y, Gallagher P, Milne K, et al. Hyperspectral cell sociology reveals spatial tumor-immune cell interactions associated with lung cancer recurrence. J Immunother Cancer. 2019 Jan. 16; 7(1):13.

15. Guerrero-Pena F A, Marrero Fernandez P D, Ing Ren T, Yui M, Rothenberg E, Cunha A. Multiclass weighted loss for instance segmentation of cluttered cells. 2018 25th IEEE International Conference on Image Processing (ICIP). IEEE; 2018. p. 2451-2455.

16. Palcic B, Garner D M, Beveridge J, Sun X R, Doudkine A, MacAulay C, et al. Increase of sensitivity of sputum cytology using high-resolution image cytometry: field study results. Cytometry. 2002 Jun. 15; 50(3):168-176.

17. Li G, Guillaud M, LeRiche J, McWilliams A, Gazdar A, Lam S, et al. Automated sputum cytometry for detection of intraepithelial neoplasias in the lung. Analytical Cellular Pathology. 2012; 35(3):187-201.

18. Macaulay C, Poh C F, Guillaud M, Michele Williams P, Laronde D M, Zhang L, et al. High throughput image cytometry for detection of suspicious lesions in the oral cavity. J Biomed Opt. 2012 August; 17(8):086004-086001.

19. Keyes M, Macaulay C, Hayes M, Korbelik J, Morris W J, Palcic B. DNA ploidy measured on archived pretreatment biopsy material may correlate with prostate-specific antigen recurrence after prostate brachytherapy. Int J Radiat Oncol Biol Phys. 2013 Aug. 1; 86(5):829-834.

20. Chiu D H K, Guillaud M, Cox D D, Follen M, MacAulay C. [PDF] Quality Assurance System Using Statistical Process Control: An Implementation for Image Cytometry—Semantic Scholar. undefined. 2004;

21. Ikeda N, MacAulay C, Lam S, LeRiche J, Payne P, Garner D, et al. Malignancy associated changes in bronchial epithelial cells and clinical application as a biomarker. Lung Cancer. 1998 March; 19(3):161-166.

22. Anderson G, Macaulay C, Matisic J, Garner D, Palcic B. The use of an automated image cytometer for screening and quantitative assessment of cervical lesions in the British Columbia Cervical Smear Screening Programme. Cytopathology. 1997 October; 8(5):298-312.

23. C Palcic B, Garner D, MacAulay C, Matisic J and Anderson D. Oncometrics Imaging Corp. and Xillix Technologies Corp.: Use of the Cyto-Savant in quantitative cytology. Acta Cytologica 40(1):67-72, 1996.

24. Kamalov R, Haskins D, Guillaud M, Harrison A, Kemp R, Chiu D, Follen M, MacAulay C. A Java Application for Tissue Section Image Analysis. Computer Methods in Programs in Biomedicine, 77(2):99-113, 2005.

25. Levenson R, Beechem J, McNamara G. Spectral imaging in preclinical research and clinical pathology. Stud Health Technol Inform. 2013; 185:43-75.

26. Erin A Marshall, Katey S S Enfield, Kevin W Ng, Martial Guillaud, Calum MacAulay, and Wan L Lam. Establishing a cell sociology platform for the assessment of targetable interactions to predict lung cancer outcome. IALC, 2019 World Lung conference, September 7-10, Barcelona, Spain. https://library.iaslc.orgiconference-program?product_id=15&author=&category=&date=&session_type=&session=&

27. E-Guillaud M, Zhang L, Poh C, Rosin M, MacAulay C. Potential use of Quantitative Tissue Phenotype to Predict Malignant Risk for Oral Premalignant Lesions. Cancer Research 68(9):3099-3107, 2008.

28. MacAulay C, Keyes M, Hayes M, Lo A, Wang G, Guillaud M, Gleave M, Fazli L, Korbelik J, Collins C, Keyes S, Palcic B. Quantification of large scale DNA organization for predicting prostate cancer recurrence. Cytometry A. 2017 December; 91(12):1164-1174

29. Guillaud M, Ye Q, Leung S, Carraro A, Harrison A, Hayes M, Nichol A, Keyes M. Large-scale DNA organization is a prognostic marker of breast cancer survival. Med Oncol. 2017 Dec. 6; 35(1):9. doi: 10.1007/s12032-017-1068-1. PMID: 29214466.

30. Varduhi Yeghiazaryan and Irina Voiculescu*. Family of boundary overlap metrics for the evaluation of medical image segmentation. J Med Imaging (Bellingham). 2018 January; 5(1): 015006. Published online 2018 Feb. 19. doi:

31. Wang, Shidan, Ruichen Rong, Donghan M. Yang, Junya Fujimoto, Shirley Yan, Ling Cai, Lin Yang et al. "Computational staining of pathology images to study the tumor microenvironment in lung cancer." Cancer Research 80, no. 10 (2020): 2056-2066.

32. http://lce.biohpc.swmed.edu/maskrcnn/33. Aarno Oskar Vuola, Saad Ullah Akram, Juho Kannala, Mask-RCNN and U-net Ensembled for Nuclei Segmentation. arXiv: 1901.10170v1 [cs.CV] 29 Jan. 2019

What is claimed is:

1. A method for segmenting cell nuclei in medical images, the method comprising:

by a first trained machine learning algorithm processing a medical image to provide center locations of cell nuclei depicted in the medical image and outputting a plurality of patches in the medical image, each patch corresponding to one of the center locations and at least some of the patches overlapping one another in the medical image;

providing the plurality of patches output from the first trained machine learning algorithm as input to a second trained machine learning algorithm;

by the second trained machine learning algorithm processing the plurality of patches, the processing by the second trained machine learning algorithm outputting, for each of the plurality of patches, a nuclear boundary in the medical image corresponding to the corresponding one of the center locations, wherein at least a plurality of the nuclear boundaries overlap one another in the medical image; and mapping each pixel of the medical image to one or more cell nuclei or no cell nuclei based on the nuclear boundaries, wherein at least some of the pixels are mapped to multiple cell nuclei.

2. The method according to claim 1 wherein the first trained machine learning algorithm is implemented by a first convolutional neural network.

3. The method according to claim 1 wherein processing the plurality of patches comprises receiving the plurality of patches as input to a second convolutional neural network.

4. The method according to claim 3 wherein the first trained machine learning algorithm is implemented by a first convolutional neural network and at least one of the first and second convolutional neural networks has a UNet configuration.

5. The method according to claim 1 wherein the plurality of patches is centered on the corresponding one of the center locations.

6. The method according to claim 1 wherein the plurality of patches of a digital histopathology representation have dimensions of at least 80 by 80 pixels.

7. The method according to claim 1 wherein the first trained machine learning algorithm is implemented by a first convolutional neural network, the second trained machine learning algorithm is implemented by a second convolutional neural network and the first and second convolutional neural networks have architectures that are one of different from one another and the same as one another.

8. The method according to claim 1 further comprising obtaining cell information corresponding to the center locations and processing the cell information together with the center locations to perform cell type based cell-cell association quantification.

9. The method according to claim 8 wherein the cell information comprises morphologically based and/or immunohistochemistry (IHC) based characterization information.

10. The method according to claim 1 wherein the medical image comprises: a digital histopathology representation, a cytology image, a cytopathology image, or an in vivo histology image.

11. The method according to claim 1 wherein the medical image includes one or more clusters of overlapping cell nuclei.

12. The method according to claim 1 comprising applying feature calculations and a binary classification tree to classify objects corresponding to the nuclear boundaries.

13. Apparatus for segmenting cell nuclei in medical images, the apparatus comprising a processor, the processor configured to:

by a first trained machine learning algorithm implemented by the processor, process a medical image to provide center locations of cell nuclei depicted in the medical image and output a plurality patches, each patch corresponding to one of the center locations and at least some of the patches overlapping one another in the medical image;

provide the plurality of patches output from the first trained machine learning algorithm as input to a second trained machine learning algorithm implemented by the processor;

by the second trained machine learning algorithm implemented by the processor, process the plurality of patches, the processing by the second trained machine learning algorithm outputting, for the plurality of patches, a nuclear boundary in the medical image corresponding to the corresponding one of the center locations, wherein at least a plurality of the nuclear boundaries overlap one another in the medical image; and mapping each pixel of each medical image to one or more cell nuclei or no cell nuclei, wherein at least some of the pixels are mapped to multiple cell nuclei.

14. The apparatus according to claim 13 wherein the first trained machine learning algorithm is implemented by a first convolutional neural network.

15. The apparatus according to claim 13 wherein the second trained machine learning algorithm is configured to receive the plurality of patches as input to a second convolutional neural network.

16. The apparatus according to claim 13 wherein the plurality of patches is centered on the corresponding one of the center locations.

17. The apparatus according to claim 13 wherein the plurality of patches of a digital histopathology representation have dimensions of at least 80 by 80 pixels.

18. The apparatus according to claim 13 wherein the first trained machine learning algorithm is implemented by a first convolutional neural network, the second trained machine learning algorithm is implemented by a second convolutional neural network and the first and second convolutional neural networks have architectures that are one of different from one another and the same as one another.

19. The apparatus according to claim 13 wherein the processor is configured to obtain cell information corresponding to the center locations and to process the cell information together with the center locations to perform cell type based cell-cell association quantification.

20. The apparatus according to claim 19 wherein the cell information comprises morphologically based and/or immunohistochemistry (IHC) based characterization information.

21. The apparatus according to claim 13 wherein the medical image comprises: a digital histopathology representation, a cytology image, a cytopathology image, or an in vivo histology image.

22. The apparatus according to claim 13 wherein the apparatus is operable to instance segment individual cell nuclei in one or more clusters of overlapping cell nuclei included in the medical image.

23. The apparatus according to claim 13 wherein the processor is configured to apply one or more feature calculations and a binary classification tree to classify objects corresponding to the nuclear boundaries.

* * * * *